United States Statutory Invention Registration [19]

[11] Reg. Number: H447

Fischer et al.

[43] Published: Mar. 1, 1988

[54] SYNTHESIS OF 1,3,5-TRINITRO-1,3,5-TRIAZACYCLOHEXANE

[75] Inventors: John W. Fischer; Ronald L. Atkins, both of Ridgecrest, Calif.

[73] Assignee: The United States of America as represented by the Secretary of the Navy, Washington, D.C.

[21] Appl. No.: 24,437

[22] Filed: Mar. 11, 1987

[51] Int. Cl.[4] ..... C07D 251/06

[52] U.S. Cl. ..... 544/180; 44/63

[56] References Cited

U.S. PATENT DOCUMENTS

| | | | |
|---|---|---|---|
| 2,355,770 | 8/1944 | Wyler | 260/248 |
| 2,398,080 | 4/1946 | Caesar | 260/248 |

*Primary Examiner*—Edward A. Miller

*Assistant Examiner*—Susan Wolffe

*Attorney, Agent, or Firm*—William C. Townsend; W. Thom Skeer

[57] ABSTRACT

A process of preparing 1,3,5-trinitro-1,3,5-triazacyclohexane of high technical purity by a one-step direct liquid nitrolysis of hexamethylenetetramine with dinitrogen pentoxide in 100% nitric acid under a separate chlorinated hydrocarbon phase.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SYNTHESIS OF 1,3,5-TRINITRO-1,3,5-TRIAZACYCLOHEXANE

BACKGROUND OF THE INVENTION

1. Field of the Invention

This invention relates to a method of preparing pure 1,3,5-trinitro-1,3,5-triazacyclohexane by the direct liquid phase nitration of hexamethylenetetramine.

2. Description of the Prior Art 1,3,5-trinitro-1,3,5-triazacyclohexane is currently prepared by a two-step procedure known in the art as the Bachman process. In this process, a mixture of ammonium nitrate and hexamine nitrate is added to a solution of nitric acid in acetic anhydride. While the product yield is about 70%, the intermediates and the final product contain about 10% of the contaminant 1,3,5,7-tetraaza-1,3,5,7-tetranitrocyclooctane. Further purification steps are required to reduce the presence of the contaminant to acceptable levels. These purification steps diminish the final yield of 1,3,5-trinitro-1,3,5-triazacyclohexane.

It is also known to prepare 1,3,5-trinitro-1,3,5-triazacyclohexane by direct liquid nitration using dinitrogen pentoxide dissolved in a non-aqueous neutral solvent such as a hydrocarbon or halogenated hydrocarbon. Although the process has been described as producing relatively pure 1,3,5-trinitro-1,3,5-triazacyclohexane, the use of a hydrocarbon or halogenated hydrocarbon solvent results in impurities which must be removed by additional processing. Additionally, scale-up problems are caused by the limited half-life of didinitrogen pentoxide in hydrocarbon or halogenated hydrocarbon solvents.

The nitration of hexamethylenetetramine to produce 1,3,5-trinitro-1,3,5-triazacyclohexane has also been achieved using concentrated nitric acid and small amounts of ammonium salts such as $NH_4NO_3$ and $(NH_4)_2SO_4$ to prevent runaway reaction and reduce the decomposition of the 1,3,5-trinitro-1,3,5-triazacyclohexane to undesirable by-products.

SUMMARY OF THE INVENTION

One object of this invention is an improved and more economical synthesis of 1,3,5-trinitro-1,3,5-triazacyclohexane.

A further object of this invention is an economical synthesis of 1,3,5-trinitro-1,3,5-triazacyclohexane of high technical purity for use an important constituent in solid propellant and explosive formulations.

According to the present invention, 1,3,5-trinitro-1,3,5-triazacyclohexane of high technical purity is synthesized by the reaction of hexamethylenetetramine with dinitrogen pentoxide in 100% nitric acid under a separate organic phase.

DETAILED DESCRIPTION OF THE INVENTION

The method of the present invention for preparing 1,3,5trinitro-1,3,5-triazacyclohexane of high technical purity provides particular advantages over existing methods. The nitrating agent $N_2O_5$ in 100% $HNO_3$ is stable indefinitely when kept at low temperatures near 0° C. under a separate chlorinated hydrocarbon phase.

Additionally, the method produces pure 1,3,5trinitro-1,3,5triazacyclohexane with no trace of 1,3,5,7-tetraaza-1,3,5,7tetranitrocyclooctane contaminent requiring removal with additional steps. Both features provide for easy and economical scale-up.

The improved synthesis of 1,3,5-trinitro-1,3,5-triazacyclohexane proceeds via nitrolysis of hexamethylenetetramine. The nitrating agent is a solution of about 20% to about 30% by weight $N_2O_5$ in 100% $HNO_3$. The hexamethylenetetramine is then added slowly to the nitrating solution kept at −20° C. under a separate chlorinated hydrocarbon phase. The reagent are mixed for a sufficient time for the nitrolysis reaction to go to completion. After that time, the 1,3,5-trinitro-1,3,5-triazacyclohexane formed is extracted from this solution into ethyl acetate. After drying and solvent removal, the pure product is isolated under vacuum.

The following example is given to illustrate but not limit the invention.

EXAMPLE

Hexamethylenetetramine (0.5 g, 3.6 mmol) was added in portions over 5 minutes to a stirred solution of 25% $N_2O_5/HNO_3$ (36 ml, 142 mmol $N_2O_2$) under $CCl_4$ (20 Ml) kept at −20° C. After 30 minutes, the yellow mixture was carefully poured onto ice (50 g), neutralized with $NaHCO_3$ and extracted into ethyl acetate. After drying with $MgSO_4$ and solvent removal under vacuum, 0.46 g of a white solid was isolated. This solid was shown to be pure 1,3,5-trinitro-1,3,5-triazacyclohexane by comparison with an authentic sample. The yield of this procedure was 57%. No trace of 1,3,5,7-tetraaza-1,3,5,7-tetranitrocyclooctane was found upon analysis by 200 MHz $^1H$ NMR.

Modifications and variations of the present invention are possible. It should be understood that, within the scope of the appended calims, the invention may be practiced otherwise than as specifically described.

What is claimed is:

1. A process of preparing pure 1,3,5-trinitro-1,3,5-triaza cyclohexane having the step of reacting hexamethylenetetramine with dinitrogen pentoxide as a primary nitrating agent, the improvement comprising the steps of:

dissolving dinitrogen pentoxide in 100% nitric acid to form a nitrating solution;

contacting said nitrating solution with hexamethylenetetramine under nitrating conditions;

neutralizing said mixture with sodium bicarbonate and extracting said product with a suitable solvent; and removing said solvent and isolating pure 1,3,5-trinitro-1,3,5-triazacyclohexane.

2. A process as in claim 1 wherein said nitrating solution comprises about 25% by weight dinitrogen pentoxide in 100% nitric acid.

3. A process as in claim 1 wherein contacting of said nitrating solution with hexamethylenetetramine comprises stirring said hexamethylenetetramine into said nitrating solution kept at −20° C. under a separate $CCl_4$ phase.

4. A process as in claim 1 wherein said solvent for extracting said product is ethyl acetate.

* * * * *